Figure 1:
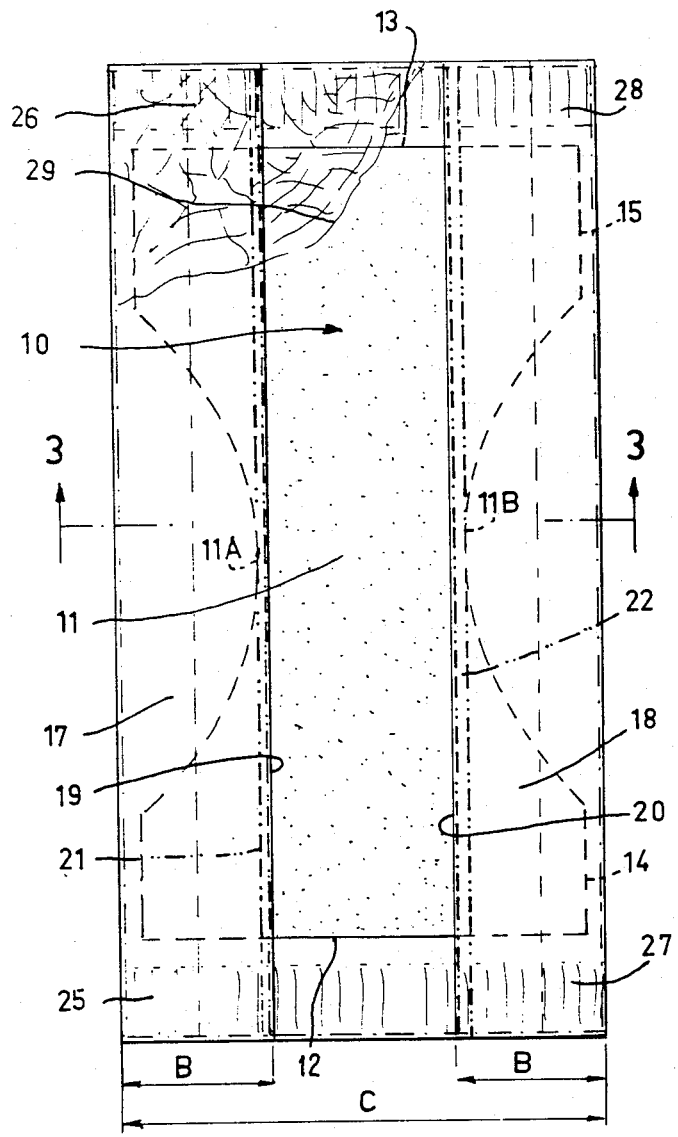

United States Patent [19]

Beckeström

[11] Patent Number: 4,490,148
[45] Date of Patent: Dec. 25, 1984

[54] PROTECTOR AGAINST INCONTINENCE OR DIAPER

[75] Inventor: Bo Beckeström, Vällingby, Sweden

[73] Assignee: Landstingens Inkopscentral, LIC, ekonomisk forening, Solna, Sweden

[21] Appl. No.: 440,947

[22] Filed: Nov. 12, 1982

[30] Foreign Application Priority Data

Jul. 1, 1982 [SE] Sweden ............................... 8204083

[51] Int. Cl.³ ............................................ A41B 13/02
[52] U.S. Cl. .................................................. 604/385
[58] Field of Search ............... 604/385, 386, 358, 398, 604/397

[56] References Cited

U.S. PATENT DOCUMENTS 3,860,003 1/1975 Buell .................................. 604/385
4,300,562 11/1981 Pieniak ............................... 604/385
4,425,127 1/1984 Suzuki et al. ....................... 604/385

Primary Examiner—John D. Yasko
Attorney, Agent, or Firm—Young & Thompson

[57] ABSTRACT

A protector against incontinence comprises an oblong absorbent body which is fixed to a bottom liquid-tight layer extending outside the absorbent body. The lateral edge portions of the layer are folded in over the absorbent body and form side flaps, the distance between the edges thereof being less than the width of the absorbent body at its mid section. The side flaps are fixed at their ends to the bottom layer. An elastic line, arranged at the edge of each side flap, tends to contract itself and thereby the edges of the side flaps. When the protector is put on, the edges of the side flaps come into elastic sealing contact in the thigh creases of the crotch.

9 Claims, 9 Drawing Figures

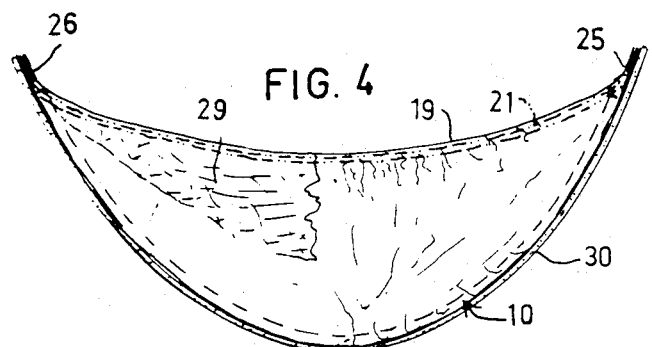
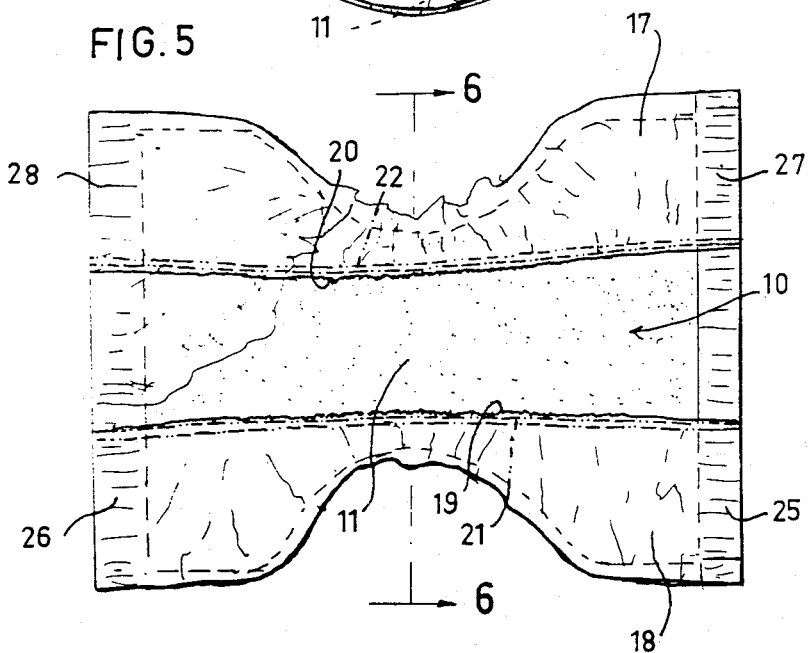
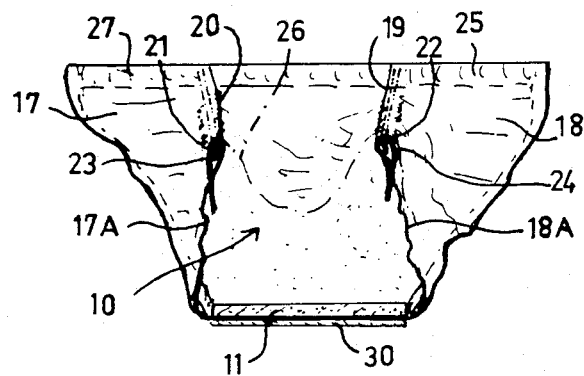

PROTECTOR AGAINST INCONTINENCE OR DIAPER

The present invention relates to a protector against incontinence or a diaper of the type disclosed in the preamble to the attached main claim.

The diaper in question of a known design consists of a bottom, liquid-tight layer such as a plastic sheet onto which the absorbent body is fixed. The bottom layer extends outside the lateral edges of the absorbent body with lateral portions provided with elastic threads, bands or corresponding elastically extensible portions running essentially longitudinally. On top of the absorbent body and the side portions, a top, liquid-permeable layer, i.e. of non-woven material, is attached. The lateral portions are made so that they can be tensioned around the thighs as the elastic portions are stretched to thereby achieve elastic contact with the thighs and improved sealing.

A disadvantage of the known diapers is, however, that they are tensioned against the thighs when in place. Movement of the thighs can then affect the position of the diaper and its sealing ability, giving rise to risk of leakage.

The purpose of the present invention is therefore to achieve a protector against incontinence or a diaper of the type in question which is designed so that the sealing contact of the elastic portions against adjacent parts of the body is, as much as possible, not affected by thigh movement.

This is achieved with a protector against incontinence or diaper which, according to the invention, has the features disclosed in the attached claims.

The protector against incontinence or the diaper according to the invention is made so that the bottom, liquid-tight layer, onto which the absorbent body is attached, has relatively wide lateral portions which are folded over to form side flaps which extend along the entire length of the diaper and are fixed at their ends to the bottom layer. In combination with the folded-in side flaps, the elastic threads, bands or corresponding elastic means are arranged at the inner, free lateral edges of the side flaps. The distance between the inner edges of the side flaps when the diaper is extended, in a suitable embodiment of the invention, is approximately equal to the width of the absorbent body at its mid section. The side flaps suitably have a width which is approximately equal to half of the width of the absorbent body at its section midway between the ends of the diaper. When the diaper is placed between the thighs, the elastic edges of the side flaps will find their way to the thigh creases of the crotch and seal against the same when the diaper is fastened in place. Usually the diaper according to the invention is held in place with a pair of briefs, which are known per se, but it is also possible to use a girdle, band, tape or the like to hold the diaper in place.

The connection between the elastically tensioned lateral edges, which are in sealing contact with the thigh creases of the crotch, and the mid section of the absorbent body consists, according to the invention, of the folded-over portions of the bottom layer, which function as easily movable bellows folds. The mid section of the absorbent body can thus make substantial movements in various directions as the bellows folds are unfolded to greater or lesser extent, without transmitting these movements to the sealing lateral edges. The seal is thereby maintained with greater security than what has been possible up to now with the protectors against incontinence or diapers in question.

By virtue of the fact that the protector or diaper according to the invention is substantially freed from the effect of leg movements, it is also more comfortable to wear than a diaper tensioned about the thighs.

A suitable embodiment of a diaper according to the invention is shown as an example in the accompanying drawings.

Figure 2:
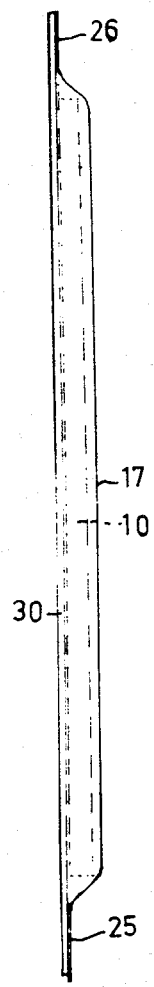
Figure 3:
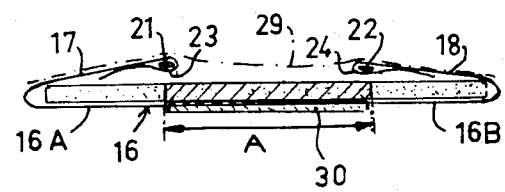

FIG. 1 is a plane view of a diaper according to the invention in the extended state, FIG. 2 is a side view, FIG. 3 is a section along the line 3—3 in FIG. 1, FIG. 4 is a side view of the diaper in the free state, in which the diaper is contracted by the elastic lines, FIG. 5 is a view from above of the diaper in FIG. 4, FIG. 6 is a section along the line 6—6 in FIG. 5, and FIGS. 7 to 9 are sections as in FIG. 3 of various modifications.

The absorbent body 10 consists of known absorbent material and, in the example shown, has a width A at its mid section 11 halfway between the ends 12,13 of the body 10. This width can vary to adapt the diaper to an adult or to an infant. In certain cases, the absorbent body can have the same width all the way out to the ends. In the example shown, however, the width increases towards the end portions 14,15, at which the width is approximately double that at the mid section 11, so that it narrows sharply to the mid section in a manner known per se.

The absorbent body 10 is fixed to a bottom liquid-tight layer 16 such as a plastic sheet, which is longer than the absorbent body and substantially wider. The lateral portions of the layer 16 are folded over inwards to form relatively wide side flaps 17,18. At their inner, free lateral edges 19,20 the side flaps are provided with elastic bands 21,22 which are shown extended in FIG. 1, while in FIGS. 4–6 they have been allowed to contract and have thereby crumpled the lateral edges 19, 20 to a shorter length.

In the example shown, the edge portions of the side flaps 17,18 are folded over and fixed with a longitudinal weld to form a tunnel 23 or 24 as shown in FIG. 3. The elastic bands 21,22 are arranged inside these tunnels and are fixed at their ends to the respective tunnel when extended.

As can be seen from FIG. 1, the ends 25,26 and 27,28 of the side flaps are fastened to the bottom layer by means of transverse welds or by other means, as indicated by the lined areas at the ends.

On top of the folded-in side flaps there is a top layer 29 of which only a portion is shown in FIGS. 1, 4 and 5. This layer consists, as is known, of liquid-permeable material such as non-woven or woven textiles, and is fixed to the ends of the diaper and to the top sides of the side flaps 17,18. A friction-increasing strip 30 is fixed to the underside of the layer 16. The strip is intended to cooperate with the briefs which are used in a known manner to hold the diaper in place.

In the example shown, the width B of the flaps 17,18 is approximately one-fourth to one-third of the width C of the diaper when extended, as shown in FIG. 1. The width of the side flaps can, however, be both larger or smaller than those values and can lie in the range of one-tenth to one-half of the width C of the diaper.

As can be seen from FIG. 1, the elastic lateral edges 19,20, when the diaper is extended, will lie approximately at the lateral edges 11A, 11B of the absorbent body 10 at its mid section 11. In this section there is thus a bellows-like fold formed by a free side portion 16A, 16B of the bottom layer 16 outside the edges 11A, 11B and the side flap 17 and 18.

When the diaper is released and is allowed to contract as shown in FIGS. 4–6, the folds will be unfolded so that the mid section 11 of the absorbent body will hang between two folded-out side portions 17A, 18A.

When the diaper is grasped at its ends and pulled up between the thighs to the position for use, the elastic edges 19,20 will come into sealing and elastic contact with the thigh creases in the crotch. Then a pair of briefs is put on which presses the absorbent body into the crotch between the legs. The side portions 17A, 18A will be folded up thereby to a greater or lesser extent and form a movable connection between the lateral edges 19,20 and the mid section 11 of the body 10, so that it can move relatively freely without affecting the lateral edges 19,20 and their seal.

Figure 7:
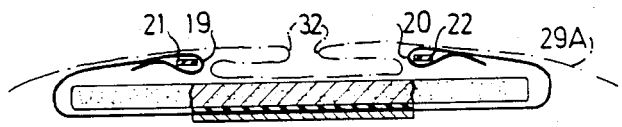

The embodiment shown in FIG. 7 differs from that shown in FIGS. 1 to 3 merely in that the non-woven layer 29A has a number of folds 32 between the lateral edges 19,20 to provide a spacious bag for penis.

Figure 8:
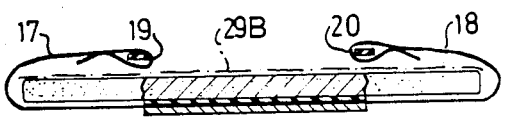

The embodiment in FIG. 8 has a non-woven layer 29B placed on the absorbent body and extending to its side edges so that the side flaps 17,18 are freely movable relative to the non-woven layer 29B so as to enable penis to be freely movable towards the absorbent body.

Figure 9:
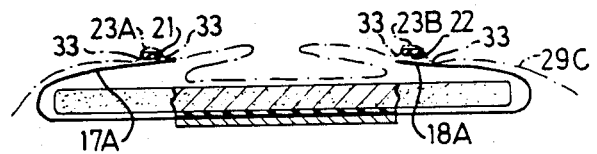

The embodiment in FIG. 9 illustrates that the elastic bands or strings 21,22 are enclosed in tunnels 23A,23B formed by the non-woven layer 29C which is welded or glued to the side flaps 17A,18A on either side of the respective elastic band 21 and 22 at lines 33 to form the tunnels.

What I claim is:

1. Protector against incontinence or diaper which when extended has an essentially rectangular shape and which comprises a bottom, liquid-tight layer such as a plastic sheet, which carries an oblong absorbent body fixed to the bottom layer, the bottom layer being provided with longitudinal elastic lines such as elastic threads, bands or lines of elastic coating arranged along at least a portion of the length of the protector to gather together the protector in the free state by elastic contraction of the elastic portions and to effect elastic and sealing contact with adjacent bodily parts in the position for use, characterized in that the bottom layer is extended to the sides with side flaps which are folded in over the bottom layer, that said side flaps are fastened at their end portions to the bottom layer, and that the elastic lines are arranged at the free edges of the side flaps.

2. Protector as claimed in claim 1, characterized in that the width of the absorbent body in its mid section between the ends of the protector is substantially less than the width of the protector.

3. Protector as claimed in claim 1, characterized in that a top layer, known per se, of liquid-permeable material such as woven or non-woven textile, is fixed onto the top sides of the folded-in side flaps.

4. Protector as claimed in claim 1, characterized in that the edges of the side flaps are each made with a tunnel in which there is an elastic thread or an elastic band which is fixed at its end portions to the tunnel.

5. Protector as claimed in claim 1, characterized in that the width of the side flaps lies in the range of one-tenth to one-half of the width of the protector when extended, preferably in the range of one-third to one-fourth of said width.

6. Protector as claimed in claim 1, characterized in that the absorbent body has essentially the same width along its entire length.

7. Protector as claimed in claim 1, characterized in that the absorbent body has a narrow mid section and has substantially wider end portions.

8. Protector as claimed in claim 3, characterized in that the top layer is folded forth and back at its middle portion between the free edges of the side flaps.

9. Protector as claimed in claim 3, characterized in that the top layer such as non-woven is sealed along two parallel spaced lines to the edge portion of the respective side flap to provide a tunnel in which the respective elastic thread, band or the like is guided and fixed at its ends to the respective side flap.

* * * * *

REEXAMINATION CERTIFICATE (592nd)
United States Patent [19]
Beckeström

[11] B1 4,490,148
[45] Certificate Issued Nov. 18, 1986

[54] PROTECTOR AGAINST INCONTINENCE OR DIAPER

[75] Inventor: Bo Beckeström, Vällingby, Sweden

[73] Assignee: Landstingens Inkopscentral, LIC, ekonomisk forening, Solna, Sweden

Reexamination Request:
No. 90/000,927, Dec. 20, 1985

Reexamination Certificate for:
Patent No.: 4,490,148
Issued: Dec. 25, 1984
Appl. No.: 440,947
Filed: Nov. 12, 1982

[30] Foreign Application Priority Data
Jul. 1, 1982 [SE] Sweden .......................... 8204083

[51] Int. Cl.⁴ ............................................. A61F 13/16
[52] U.S. Cl. ................................................ 604/385.2
[58] Field of Search ................ 604/385.1, 385.2, 386, 604/358, 393, 394, 397, 398

[56] References Cited
U.S. PATENT DOCUMENTS

| | | |
|---|---|---|
| 3,452,753 | 7/1969 | Sanford . |
| 3,572,342 | 3/1971 | Lindquist et al. . |
| 3,860,003 | 1/1975 | Buell . |
| 3,952,745 | 4/1976 | Duncan . |
| 4,210,144 | 7/1980 | Sarge, III et al. . |

*Primary Examiner*—John D. Yasko

[57] ABSTRACT

A protector against incontinence comprises an oblong absorbent body which is fixed to a bottom liquid-tight layer extending outside the absorbent body. The lateral edge portions of the layer are folded in over the absorbent body and form side flaps, the distance between the edges thereof being less than the width of the absorbent body at its mid section. The side flaps are fixed at their ends to the bottom layer. An elastic line, arranged at the edge of each side flap, tends to contract itself and thereby the edges of the side flaps. When the protector is put on, the edges of the side flaps come into elastic sealing contact in the thigh creases of the crotch.

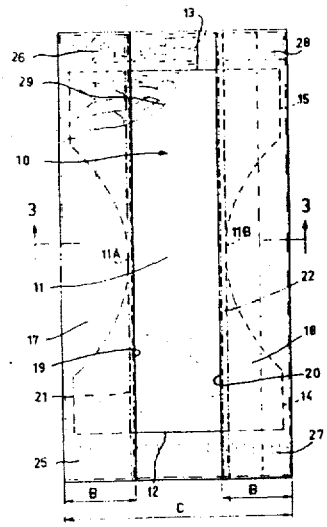

REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but as been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–9, dependent on an amended claim, are determined to be patentable.

1. Protector against incontinence or diaper which when extended has an essentially rectangular shape and which comprises a bottom, liquid-tight layer such as a plastic sheet, which carries an oblong absorbent body fixed to the bottom layer, the bottom layer being provided with longitudinal elastic lines such as elastic threads, bands or lines of elastic coating arranged along at least a portion of the length of the protector to gather together the protector in the free state by elastic contraction of the elastic portions and to effect elastic and sealing contact with adjacent bodily parts in the position for use, characterized in that the bottom layer is extended to the sides with side flaps which are folded in over the bottom layer *and over the longitudinal sides of the oblong absorbent body, the bottom layer being extended endwise by ends that are disposed endwise beyond the ends of the oblong absorbent body*, that said *folded over* side flaps are fastened at their end portions to *said extended ends of* the bottom layer *at locations intermediate the width of the protector*, and that the elastic lines are arranged at the free edges of the side flaps *and are each fixed at both their ends to the side flaps endwise beyond the ends of the absorbent body at locations intermediate the width of the protector.*

* * * * *